US008194952B2

(12) United States Patent
Mertz et al.

(10) Patent No.: US 8,194,952 B2
(45) Date of Patent: Jun. 5, 2012

(54) IMAGE PROCESSING SYSTEM AND METHODS FOR ALIGNING SKIN FEATURES FOR EARLY SKIN CANCER DETECTION SYSTEMS

(75) Inventors: Frederick C. Mertz, San Diego, CA (US); Robert K. Pina, Ramona, CA (US); Ivans S. Chou, Chula Vista, CA (US); Karleen Seybold, Tucson, AZ (US)

(73) Assignee: Raytheon Company, Waltham, MA (US)

( * ) Notice: Subject to any disclaimer, the term of this patent is extended or adjusted under 35 U.S.C. 154(b) by 936 days.

(21) Appl. No.: 12/133,163

(22) Filed: Jun. 4, 2008

(65) Prior Publication Data
US 2009/0304243 A1 Dec. 10, 2009

(51) Int. Cl.
G06K 9/48 (2006.01)
G06K 9/36 (2006.01)
(52) U.S. Cl. ........ 382/128; 382/174; 382/175; 382/256; 382/284; 600/407
(58) Field of Classification Search .......... 600/407–464; 382/128–133, 173–294
See application file for complete search history.

(56) References Cited

U.S. PATENT DOCUMENTS

| | | | |
|---|---|---|---|
| 6,173,275 B1 | 1/2001 | Caid et al. | |
| 6,628,805 B1 | 9/2003 | Hansen | |
| 6,959,119 B2 | 10/2005 | Hawkins et al. | |
| 6,993,167 B1 | 1/2006 | Skladnev et al. | |
| 7,162,063 B1 | 1/2007 | Craine et al. | |
| 7,657,101 B2 * | 2/2010 | Christiansen et al. | 382/218 |
| 2002/0042723 A1 | 4/2002 | Rice et al. | |
| 2002/0191028 A1 | 12/2002 | Senechalle et al. | |
| 2003/0026503 A1 | 2/2003 | Kallergi et al. | |
| 2004/0012638 A1 | 1/2004 | Donnelli et al. | |
| 2004/0093166 A1 | 5/2004 | Kil | |

(Continued)

FOREIGN PATENT DOCUMENTS
WO WO-2009148596 A1 12/2009
(Continued)

OTHER PUBLICATIONS
"International Application Serial No. PCT/US2009/003386, Search Report mailed Aug. 4, 2009", 3 pgs.
(Continued)

Primary Examiner — Melissa Koval
Assistant Examiner — Emily Chan
(74) Attorney, Agent, or Firm — Schwegman, Lundberg & Woessner, P.A.; Gregory J. Gorrie

(57) ABSTRACT

Embodiments of an image processing system and methods for aligning features suitable for use in early skin-cancer detection systems are described herein. Corresponding skin features between a reference image and a later-captured image are precisely aligned. Curvatures are used to align body outlines of corresponding images using body-background masks. An initial-displacement flowfield map, generated from the aligned body outlines, may be applied to a filtered version of the later-captured image to generate a pre-warped image. The pre-warped image and a filtered version of the reference image are divided into a plurality of overlapping chips and a correlation is performed between corresponding chips. A transformation map may be generated based on the chip correlations. This chipping process may be iterated for successively smaller chip sizes to generate a final transform map which may be applied to the later-captured image to generate a registered image having its skin features aligned with the reference image.

36 Claims, 8 Drawing Sheets

U.S. PATENT DOCUMENTS

| | | | |
|---|---|---|---|
| 2004/0161141 A1* | 8/2004 | Dewaele | 382/132 |
| 2004/0264749 A1 | 12/2004 | Skladnev et al. | |
| 2004/0267102 A1 | 12/2004 | Skladnev et al. | |
| 2005/0190980 A1 | 9/2005 | Bright | |
| 2005/0232474 A1 | 10/2005 | Wei et al. | |
| 2006/0002632 A1 | 1/2006 | Fu et al. | |
| 2006/0036412 A1 | 2/2006 | Takatsuka | |
| 2006/0120620 A1* | 6/2006 | Bassi et al. | 382/276 |
| 2006/0227385 A1 | 10/2006 | Kawada | |
| 2006/0259509 A1 | 11/2006 | Stolte et al. | |
| 2006/0291708 A1 | 12/2006 | Dehmeshki et al. | |
| 2007/0050104 A1 | 3/2007 | Wallace et al. | |
| 2007/0064989 A1 | 3/2007 | Chhibber et al. | |
| 2009/0196475 A1 | 8/2009 | Demirli et al. | |
| 2009/0327890 A1 | 12/2009 | Mertz et al. | |
| 2010/0111387 A1* | 5/2010 | Christiansen, II et al. | 382/128 |

FOREIGN PATENT DOCUMENTS

| | | | |
|---|---|---|---|
| WO | WO-2009158001 A1 | 12/2009 | |

OTHER PUBLICATIONS

"International Application Serial No. PCT/US2009/003386, Written Opinion mailed Aug. 4, 2009", 5 pgs.

"International Application Serial No. PCT/US2009/003773, Search Report mailed Aug. 12, 2009", 3 pgs.

"International Application Serial No. PCT/US2009/003773, Written Opinion mailed Aug. 12, 2009", 5 pgs.

"U.S. Appl. No. 12/147,081, Non Final Office Action mailed Sep. 13, 2011", 22 pgs.

"U.S. Appl. No. 12/147,081, Response filed Dec. 12, 2011 to Non Final Office Action mailed Sep. 13, 2011", 13 pgs.

"International Serial No. PCT/US2011/51182, International Search Report mailed Jan. 26, 2012", 2 pgs.

"International Serial No. PCT/US2011/51182, Written Opinion mailed Jan. 26, 2012", 6 pgs.

\* cited by examiner

SKIN-FEATURE CHANGE-DETECTION SYSTEM

IMAGE PROCESSING AND FEATURE ALIGNMENT SYSTEM

IMAGE PROCESSING SYSTEM AND METHODS FOR ALIGNING SKIN FEATURES FOR EARLY SKIN CANCER DETECTION SYSTEMS

TECHNICAL FIELD

Some embodiments pertain to image processing systems and systems that align skin features between two or more images. Some embodiments pertain to alignment of skin features, such as nevi, between two or more body images. Some of these embodiments pertain to early skin cancer detection systems.

BACKGROUND

Skin cancer is an increasing health problem globally with over one million new cases diagnosed each year in the United States alone, including almost 60,000 new cases of melanoma, the most serious form of skin cancer, and more than 8,000 deaths. Despite significant fundamental and clinical research efforts, the treatment of advanced melanoma has only shown minimal impact on the overall prognosis for this disease. The focus on skin cancer treatment traditionally has been on improved treatments for final stages and prevention. The statistics indicate that most resources are expended in the later stages of skin cancer where the probability is lower for a full recovery. It may be beneficial to the public and the health care insurance industries to shift resources to early skin cancer detection where probabilities increase significantly for survival and a continued productive life.

One difficulty with early skin cancer detection is that there is no objective method for skin cancer screening available for use in a clinical setting. Conventionally, skin cancer screening is performed by combining visual observations with manual handwritten tracking methods done locally in a physician's office. Digital photography has been used by some dermatologists and patients to help identify skin changes, but it remains difficult to compare baseline images to lesions observed at the time of a skin examination. One of the more important melanoma risk factors are persistently changing moles in size, and color, and the presence of a large number of moles of at least a certain diameter. The difficulty in imaging the human body over time, aligning features of the images, and comparing those images in a reliable, and clinically useful way is not currently available.

Thus, there are general needs for systems and methods for precisely aligning skin features in images captured over time and detecting changes in the skin features that may be suitable for use in early skin cancer detection.

DETAILED DESCRIPTION

The following description and the drawings sufficiently illustrate specific embodiments to enable those skilled in the art to practice them. Other embodiments may incorporate structural, logical, electrical, process, and other changes. Examples merely typify possible variations. Individual components and functions are optional unless explicitly required, and the sequence of operations may vary. Portions and features of some embodiments may be included in, or substituted for those of other embodiments. Embodiments set forth in the claims encompass all available equivalents of those claims.

Figure 1:
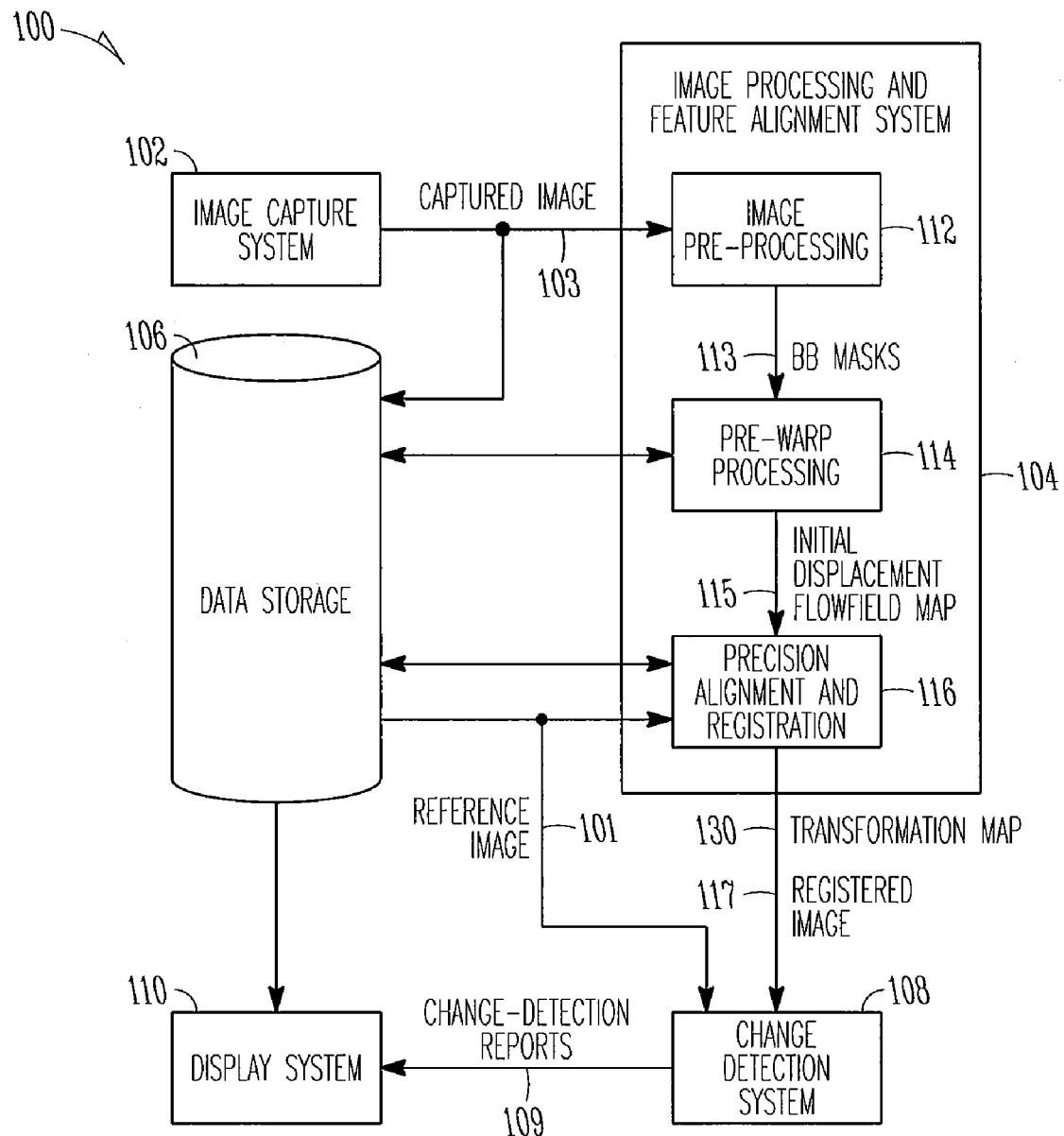
FIG. 1 is a block diagram of a skin-feature change-detection system in accordance with some embodiments.

FIG. 1 is a block diagram of a skin-feature change-detection system in accordance with some embodiments. Skin-feature change-detection system 100 may be used to capture an image and precisely align skin features with a reference image that was taken at a different time. In some embodiments, skin-feature change-detection system 100 may be used to identify changes in the skin features between the images and display the changes for analysis by a physician, although the scope of the embodiments is not limited in this respect.

Skin-feature change-detection system 100 may include image capture system 102 to capture images, and data storage 106 to store, among other things, the captured images including metadata associated with captured images 103. Skin-feature change-detection system 100 may also include image processing and feature alignment system 104 to align skin features of a captured image with features of reference image 101 to generate registered image 117 from the captured image. Registered image 117 may have its skin features aligned with corresponding skin features of reference image 101. In some embodiments, image processing and feature alignment system 104 may utilize pixel-to-pixel spatial coordinate transformation map 130 for warping coordinates of a captured image to generate registered image 117 as an output.

Skin-feature change-detection system 100 may also include change-detection system 108 to generate change-detection reports 109 which may be based on a comparison of the aligned skin features of registered image 117 and reference image 101. Skin-feature change-detection system 100 may also include display system 110, which may include a graphical user interface (GUI), to display, among other things, a comparison of the aligned skin features of registered image 117 and reference image 101. In some embodiments, change-detection reports 109 may identify skin features, such as nevi, that have changed based on predetermined criteria between reference image 101 and registered image 117. As used herein, the terms nevi and nevus refers to sharply-circumscribed and chronic lesions of the skin, which may be commonly referred to as birthmarks and moles. Nevi may or may not be benign.

In some embodiments, image processing and feature alignment system 104 may include image pre-processing module 112 to compute body-background (BB) masks 113 for corresponding images (e.g., reference image 101 and a later-captured image). Image processing and feature alignment system 104 may also include pre-warp processing module 114 to generate and align body outlines of the corresponding images based on curvatures generated from body-background masks 113 of the corresponding images. Pre-warp processing module 114 may also generate initial displacement flowfield map 115, which may be used to align coordinates of the body outlines. The term 'body-outline' may refer to an outline of any object including a full human body, portions of human bodies (e.g., hands, feet, arms, shoulders) as well as non-human objects.

Image processing and feature alignment system 104 may also include precision alignment and registration module 116 to apply initial displacement flowfield map 115 to a filtered version of one of the images to achieve a gross-alignment of the corresponding images and to generate a pre-warped image. The filtered version of the images used by precision alignment and registration module 116 may be generated by an image filter discussed below. Precision alignment and registration module 116 may also divide the filtered versions of the pre-warped image and the reference image into a plurality of chips, perform a correlation between corresponding chips of the corresponding images, and generate pixel-to-pixel spatial coordinate transformation map 130 that aligns features between the corresponding images. In some embodiments, this chipping process may be iterated for successively smaller chip sizes, each time applying a newly-generated transformation map until a final transformation map is generated. The final transformation map may be applied to a later-captured image to generate registered image 117 having its skin features aligned with reference image 101. These embodiments are discussed in more detail below. In some embodiments, precision alignment and registration module 116 may divide the filtered versions of the pre-warped image and the reference image into a plurality of overlapping chips, however non-overlapping chips may also be used.

In some embodiments, rather than providing registered image 117 as an output, image processing and feature alignment system 104 may provide the final pixel-to-pixel spatial coordinate transformation map as an output. The final pixel-to-pixel spatial coordinate transformation map may then be used to warp coordinates of a captured image to generate the registered image.

Figure 2:
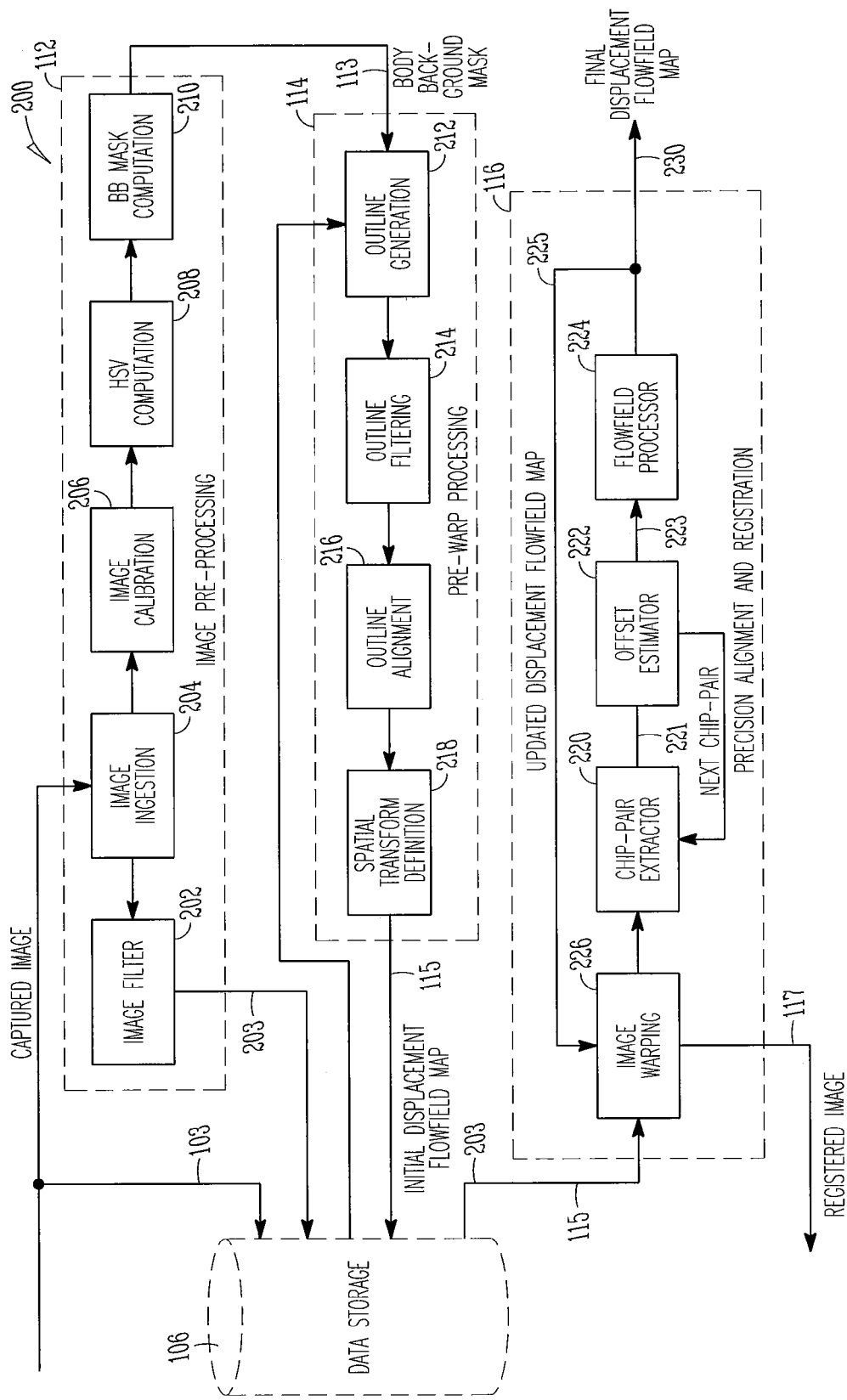
FIG. 2 is a block diagram of an image processing and feature alignment system in accordance with some embodiments.

FIG. 2 is a block diagram of an image processing and feature alignment system in accordance with some embodiments. Image processing and feature alignment system 200 may be configured to align skin features, such as nevi, between two or more corresponding images, such as a reference image and a later-captured image. As illustrated in FIG. 2, image processing and feature alignment system 200 may be suitable for use as image processing and feature alignment system 104 (FIG. 1) and may comprise image preprocessing module 112, pre-warp processing module 114, and precision alignment and registration module 116, the various elements of which are discussed in more detail below.

Figure 3A:
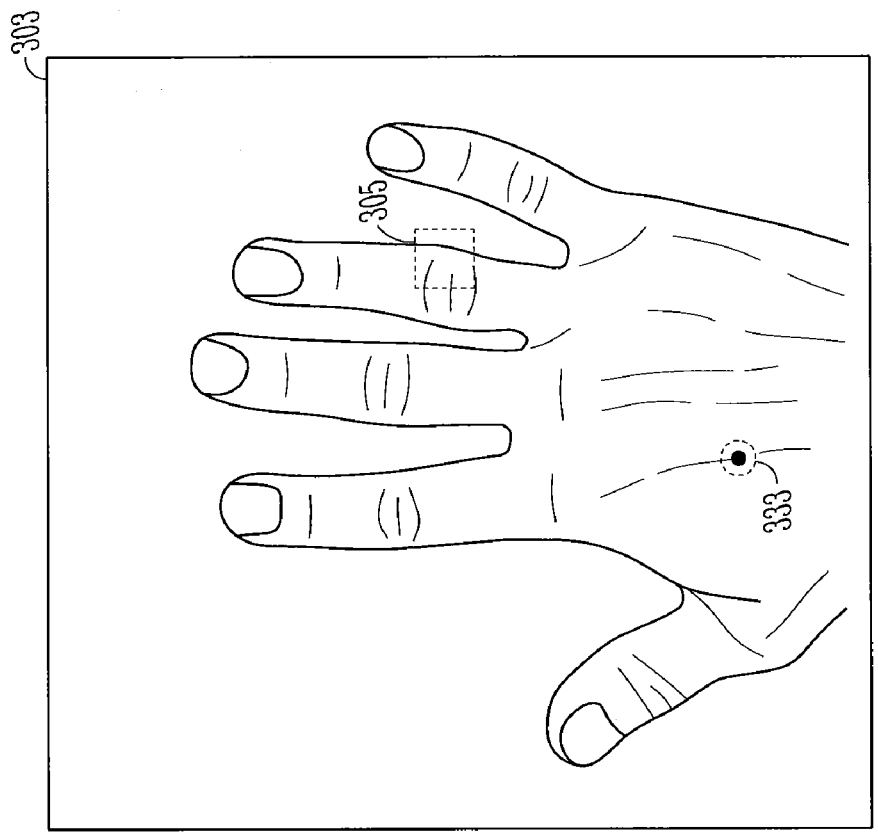
FIG. 3A are sketches of a pair of unregistered images.
Figure 3A:
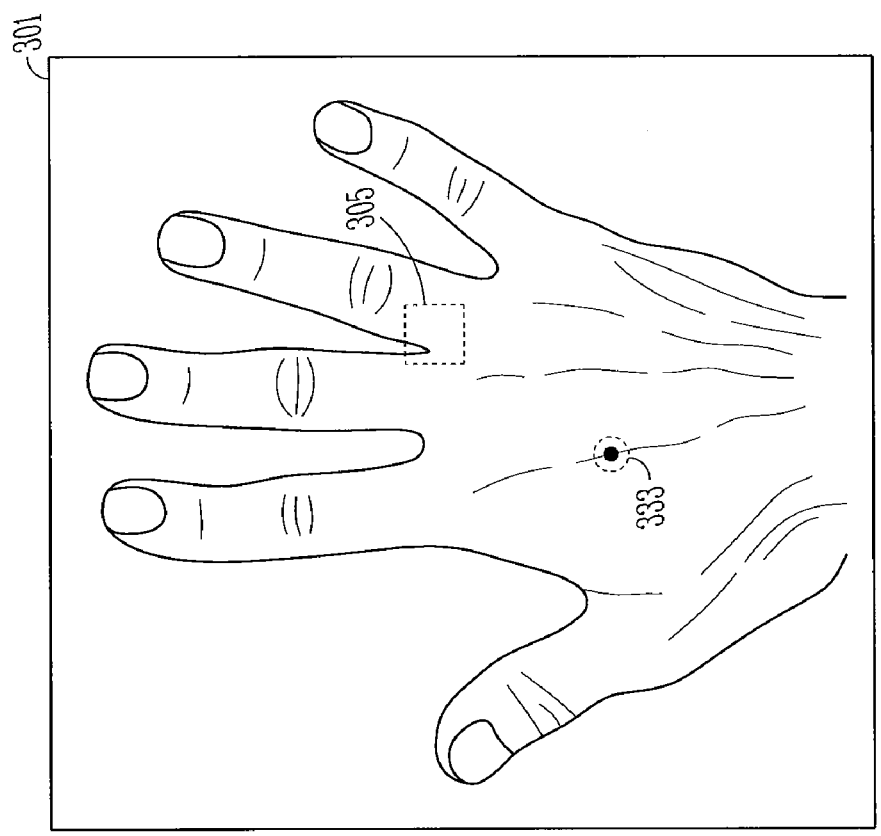

FIG. 3A are sketches of a pair of unregistered images that may include reference image 301 and later-captured image 303. Reference image 301 and later-captured image 303 are corresponding images that may have been captured at different times. The images within the frames of reference image 301 and later-captured image 303 are not necessarily aligned (e.g., later-captured image 303 is lower within the photographic framing). Furthermore, the body outlines of reference image 301 and later-captured image 303 are not necessarily aligned (e.g., one image may be slightly rotated resulting in a slightly different body outline), and features within the images are not necessarily aligned. For example, boxes 305 that have the same x-y coordinates within image 301 and image 303 do not necessarily include the same features of the images because later-captured image 303 is not yet registered. Since images 301 and 303 are unregistered, corresponding skin features, such as skin feature 333, are not necessarily aligned.

In some embodiments, the pixel-to-pixel spatial coordinate transformation map generated by precision alignment and registration module 116 (FIG. 1) may be used to warp one image (e.g., later-captured image 303) to another image (e.g., reference image 301) to align the corresponding features. After precision alignment and registration, corresponding skin features present in the image pairs may be aligned. For example, after precision alignment and registration, skin feature 333 in reference image 301 may reside at the same x-y location the registered image.

Figure 3B:
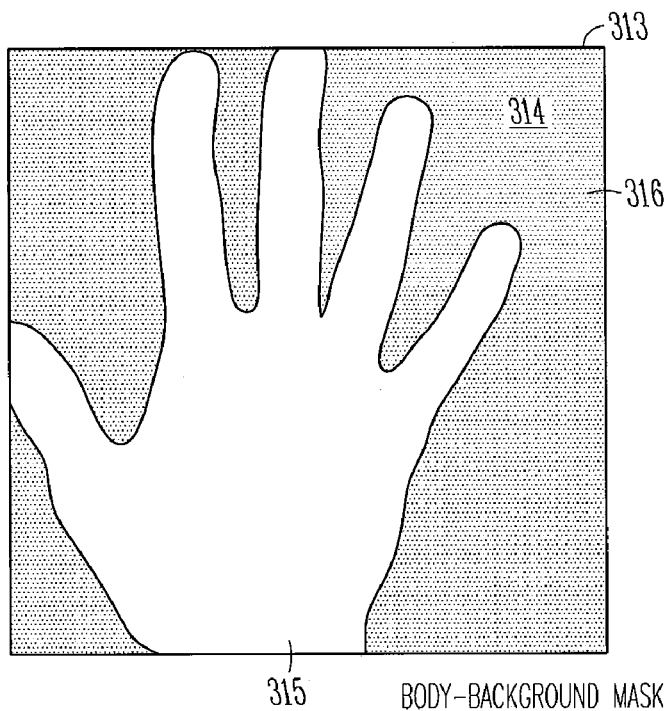
FIG. 3B illustrates a body-background mask in accordance with some embodiments.

FIG. 3B illustrates a body-background mask in accordance with some embodiments. Image pre-processing module 112 (FIG. 2) may compute body-background mask 313 for each of the corresponding images by separating non-background pixels 315 from background pixels 316 in the images. This may be done based on a predetermined background color of background region 314 used in the image-capture process.

Figure 3C:
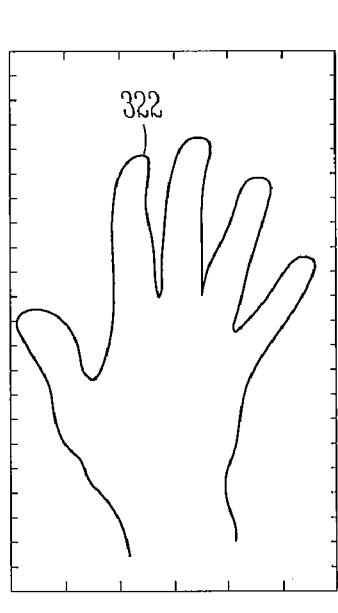
FIG. 3C illustrates a body outline in accordance with some embodiments.

FIG. 3C illustrates a body outline in accordance with some embodiments. Pre-warp processing module 114 (FIG. 2) may generate a body outline, such as body outline 322, for each of the corresponding images. The use of body outlines is discussed in more detail below.

Figure 3D:
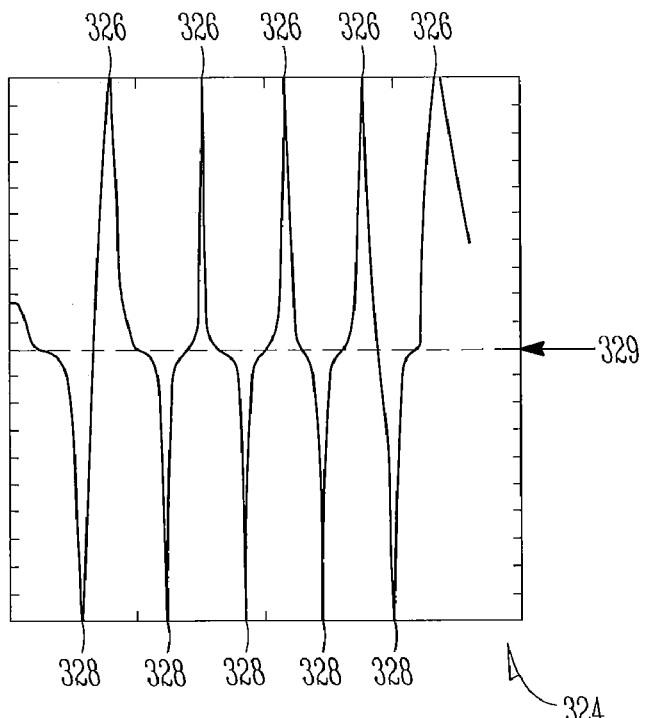
FIG. 3D illustrates a curvature plot of a body outline in accordance with some embodiments.

FIG. 3D illustrates a curvature plot of a body outline in accordance with some embodiments. Pre-warp processing module 114 (FIG. 2) may align body outlines based on curvatures of curvature plot 324 generated from body outlines of corresponding images. Curvature plot 324 may identify key features of body outline 322 (FIG. 3C). For example, points 326 of curvature plot 324 have very high positive curvature and may correspond to the portions in-between the fingers in body outline 322. Points 328 of curvature plot 324 have very high negative curvature and may correspond to the finger tips in body outline 322. In some embodiments, curvature plot 324 may be normalized, for example, with respect to zero crossings 329. This is discussed in more detail below.

Figure 3E:
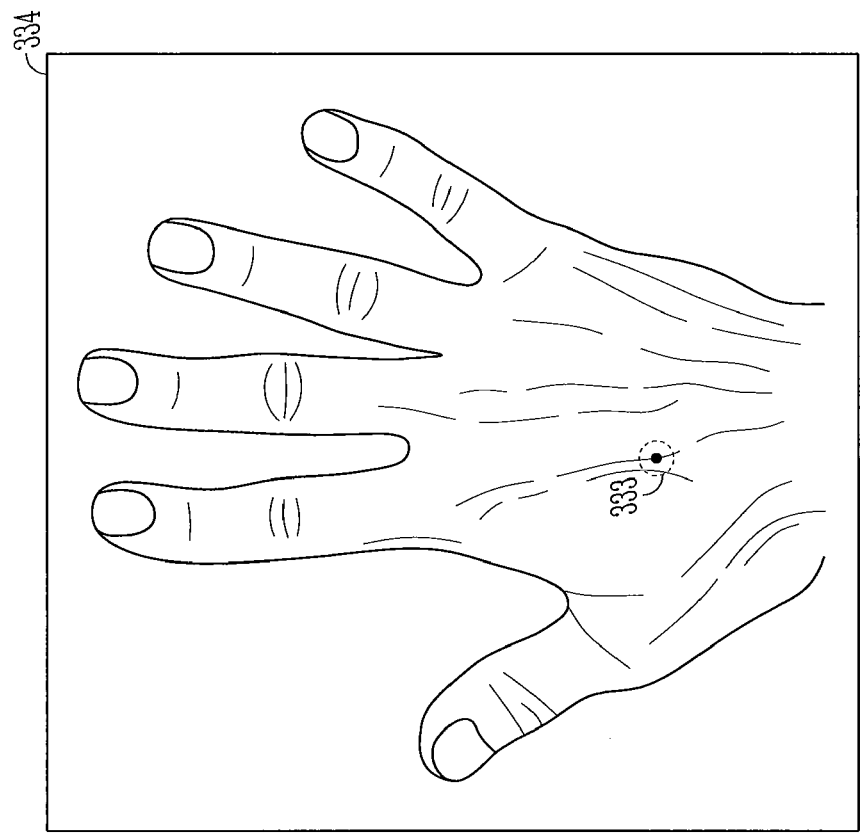
FIG. 3E are sketches of a reference image and a pre-warped image in accordance with some embodiments.
Figure 3E:
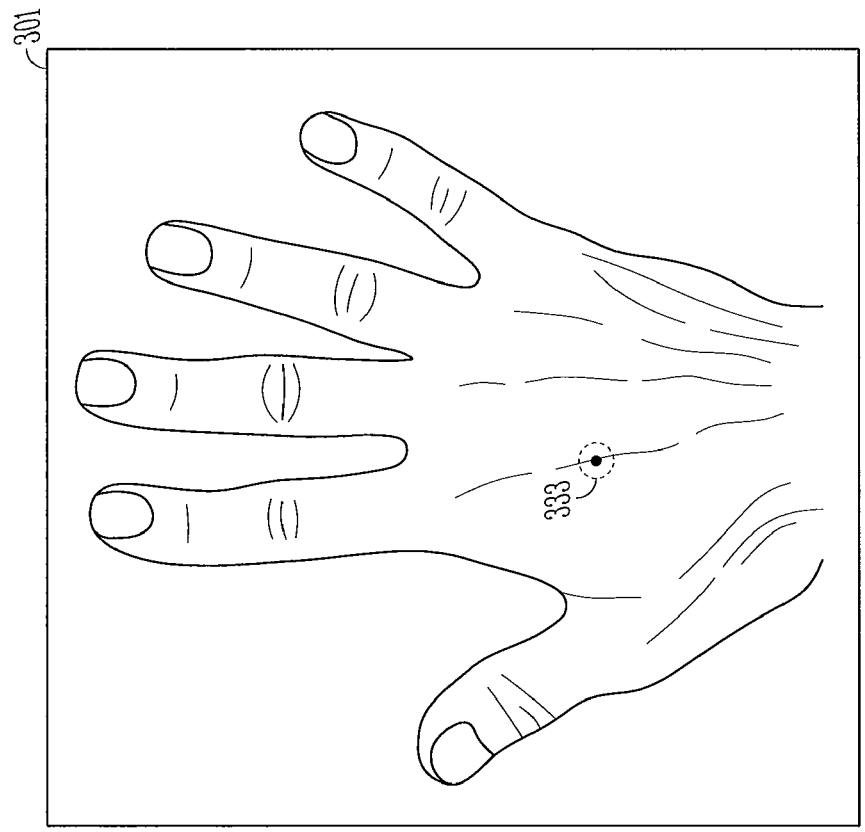

FIG. 3E are sketches of a reference image and a pre-warped image in accordance with some embodiments. Pre-warped image 334 may result from the application of initial displacement flowfield map 115 (FIG. 1) to later-captured image 303 (FIG. 3A) to align the outlines of later-captured image 303 (FIG. 3A) with reference image 301. Although the outlines of pre-warped image 334 and reference image 301 are aligned within the photographic frames, internal features, such as corresponding features 333, may not necessarily be aligned. As illustrated in FIG. 3E, corresponding features 333 are not located at the same x-y coordinates in the images. Therefore pre-warped image 334 is not considered registered.

Figure 3F:
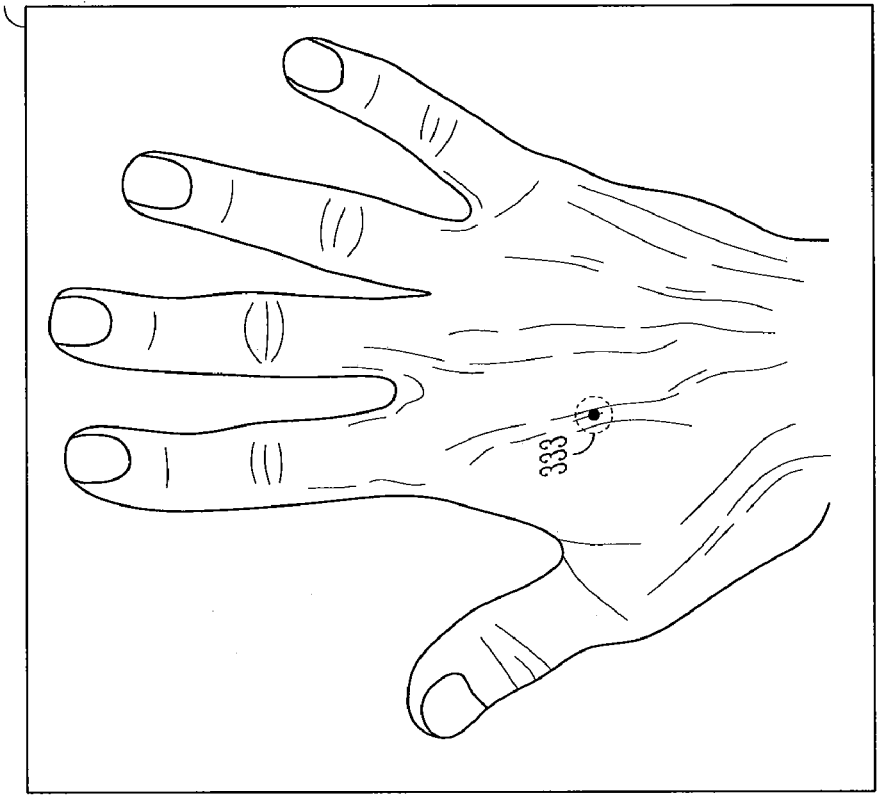
FIG. 3F are sketches of a reference image and a registered image in accordance with some embodiments.
Figure 3F:
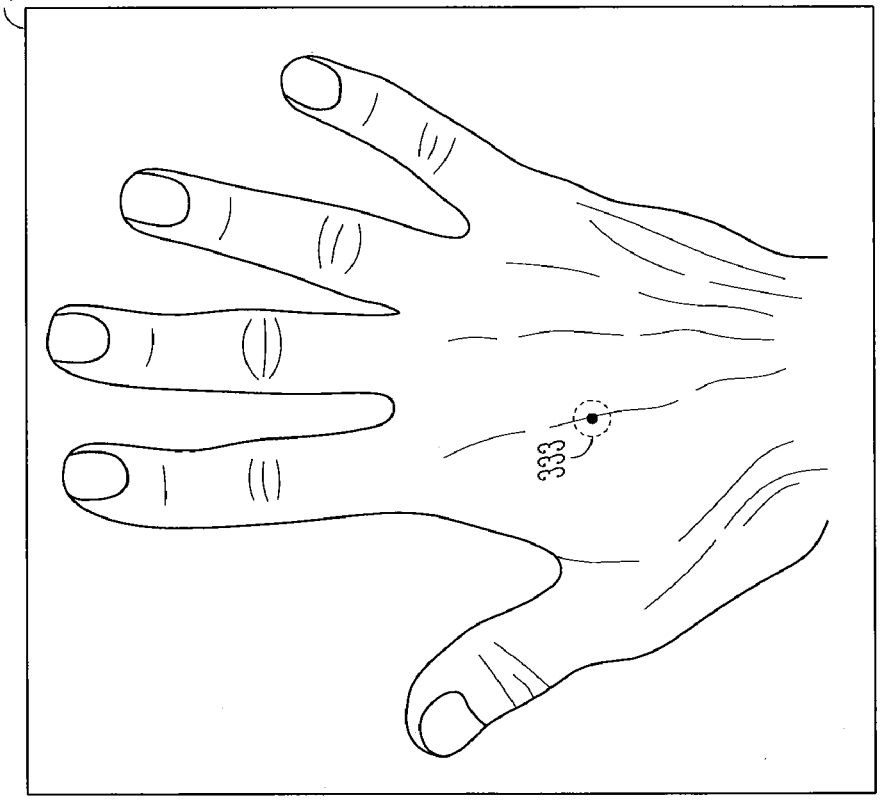

FIG. 3F are sketches of a reference image and a registered image in accordance with some embodiments. Registered image 344 may have its skin features aligned with corresponding skin features of reference image 301. The pixel-to-pixel spatial coordinate transformation map generated by precision alignment and registration module 116 (FIG. 1) may be applied directly to later-captured image 303 (FIG. 3A) to generate registered image 344. As illustrated in FIG. 3F, the corresponding skin features, such as skin features 333, of registered image 344 and reference image 301 are now aligned. The outlines of registered image 344 and reference image 301, however, may not necessarily be aligned. To clarify, the pixel-to-pixel spatial coordinate transformation map generated by precision alignment and registration module 116 (FIG. 1) may induce a misalignment of the body outline to achieve skin feature alignment. This may occur because, for example, a slight rotation of the body or body part during image capture may change the projected distance between a skin feature and the apparent edge of the body or body part. For example, while a skin feature may be the same feature in two images and is therefore aligned, the apparent edge of the body or body part may not be the same edge in both images and is therefore not aligned.

Although FIGS. 3A, 3E, and 3F are sketches of images, actual images are used by image processing and feature alignment system 104, as described in more detail below. In some embodiments, corresponding images may refer to unregistered images of the same person, body part, or object taken at different times, such as reference image 301 (FIG. 3A) and later-captured image 303 (FIG. 3A). Reference image 301 (FIG. 3A) may be an initial or archived image, and later-captured image 303 (FIG. 3A) may have been taken at a later time (e.g., days, weeks or even years later). Corresponding images may also be images of the same person, body part, or object taken of the same body pose. Unregistered images do not necessarily have their corresponding features aligned. Although FIGS. 3A, 3E, and 3F illustrate hands, the scope of the embodiments is not limited in this respect as full-body images or partial body images may also be used.

Referring to FIG. 2, image pre-processing module 112 may be configured to compute body-background mask 313 (FIG. 3B) for each of the corresponding images by separating non-background pixels 315 (FIG. 3B) from background pixels 316 (FIG. 3B) in the images based on a predetermined background color. Body-background masks may comprise binary listings of ones and zeros for each coordinate of the images in the x-y plane. In some embodiments, a body-background mask may be generated for each pose and each image in a temporal sequence of images. Non-background pixels 315 (FIG. 3B) may comprise patient pixels or object pixels. In some embodiments, the predetermined background color may be blue or a shade of blue, such as photo-blue or savage golf blue, although the scope of the embodiments is not limited in this respect.

Image pre-processing module 112 may include image filter 202 to generate a filtered version images for use by precision alignment and registration module 116. Image filter 202 may generate a spatially filtered and/or a spectrally filtered version the images. These embodiments are discussed in more detail below.

Image pre-processing module 112 may also include image ingestion module 204 to convert a captured image (e.g., reference image 301 or later-captured image 303) from a camera-raw format to a predetermined digital image processing (DIP) format. The predetermined DIP format may comprise a predetermined number of bits for each color pixel. The camera-raw format may be specific to the type of camera used to capture the image. In some embodiments, the predetermined DIP format may comprise a three-color binary format, such as a red-green-blue (R-G-B) binary format. In these embodiments, the predetermined DIP format may comprise 32-bits for each red (R) pixel, 32-bits for each green (G) pixel, and 32-bits for each blue (B) pixel, although the scope of the embodiments is not limited in this respect.

Image pre-processing module 112 may also include image calibration module 206 to color-balance the captured image after conversion to the predetermined DIP format. In some embodiments, the color-mix and color intensity may be balanced and standardized so that skin colors and background colors have about the same intensity between different images, although the scope of the embodiments is not limited in this respect.

Image pre-processing module 112 may also include hue-saturation-value (HSV) computation module 208. HSV computation module 208 may convert the color-balanced image generated by image calibration module 206 from the predetermined DIP format to HSV color space.

Image pre-processing module 112 may also include body-background (BB) mask computation module 210 to generate body-background masks, such as body-background mask 313 (FIG. 3B). Image pre-processing module 112 may separate pixels in HSV color space based on predetermined hue tolerances into background pixels 316 (FIG. 3B) and non-background pixels 315 (FIG. 3B). In these embodiments, the use of HSV color space may exploit the color (e.g., blueness of the background) so that background pixels 316 (FIG. 3B) may be easily separated from non-background pixels 315 (FIG. 3B) (i.e., body pixels). Body-background masks, such as body-background mask 313 (FIG. 3B), may be binary images represented by ones and zeros for each position in the coordinate (e.g., x-y) plane. In these embodiments, each background pixel 316 (FIG. 3B) may be represented by one value (e.g., a zero) in the coordinate plane and each non-background pixel 315 (FIG. 3B) may be represented by another value (e.g., a one) in the coordinate plane. Body-background mask 313 (FIG. 3B) is a black and white image without any shading and is devoid of color in which background pixels 316 (FIG. 3B) are shown as grey and non-background pixels 315 (FIG. 3B) are shown as white. Although body-background mask 313 (FIG. 3B) is illustrated as a mask of a hand, the scope of the embodiments is not limited in this respect as body-background mask 313 (FIG. 3B) may comprise a mask of a full-body image or a portion of the body.

At the pixel level, an initial binary body-background mask derived using the background color separation process described above may be noisy and may contain speckles of background pixels 316 (FIG. 3B) which should have been identified as non-background pixels 315 (FIG. 3B) (e.g., on-body), as well as non-background pixels 315 (FIG. 3B) in background region 314 (FIG. 3B). In some embodiments, body-background mask computation module 210 may apply spatial morphological operators to help reduce and possibly eliminate the speckles and smooth out the edge of body-background mask 313 (FIG. 3B). In these embodiments, enclosed "islands" of body or background pixels may be compared to the surrounding area to determine their correct assignment. In these embodiments, body-background mask computation module 210 may be configured to apply spatial morphological operators to initial binary body-background masks to reduce speckles and smooth edges of the initial body-background masks to generate body-background masks of the corresponding images. Body-background mask 313 (FIG. 3B) illustrates an example of the output generated by the processes performed by body-background mask computation module 210.

Referring to FIG. 2, pre-warp processing module 114 may align the body outlines of the corresponding images by matching peaks of curvature plots generated from the body outlines, and may define a spatial transform for each coordinate of one of the images based on the aligned body outlines to produce initial displacement flowfield map 115. In some embodiments, pre-warp processing module 114 may include outline-generation module 212 to generate body outlines, such as body outline 322 (FIG. 3C), for each of the corresponding images from the corresponding body-background masks. Pre-warp processing module 114 may also include outline-filtering module 214 to smooth the body outlines and to calculate a curvature plot, such as curvature plot 324 (FIG. 3D), for each of the corresponding images from the smoothed body outlines.

In some embodiments, each body outline may comprise a string of x-y coordinates (i.e., a vector) defining a boundary of the intersection between the ones and zeros of a body-background mask. For example, a contouring routine may be used to generate body outline 322 (FIG. 3C) from body-background mask 313 (FIG. 3B). In some embodiments, a body outline for each of the corresponding images may be stored as body-outline coordinate file for each of the corresponding images in data storage 106.

In some embodiments, outline-filtering module 214 may generate a curvature plot, such as curvature plot 324 (FIG. 3D), based on the curvature at each point of body outline 322 (FIG. 3C). The curvature at any given point along a curve may be defined as the inverse of the radius of the osculating circle at the given point. Curvature plot 324 (FIG. 3D) may identify key features of body outline 322 (FIG. 3C). For example, points 326 (FIG. 3D) have very high positive curvature and may correspond to the portions in-between the fingers in body outline 322 (FIG. 3C). Points 328 (FIG. 3D) have very high negative curvature and may correspond to the finger tips in body outline 322 (FIG. 3C). In some embodiments, outline-filtering module 214 may generate curvature plots for one or more archived images using body-outline coordinate files stored in data storage 106.

In some embodiments, outline-filtering module 214 may also modify curvature plots 324 by identifying zero crossings 329 (FIG. 3D) and by normalizing the curvature between each zero crossing by the maximum curvature magnitude obtained within each of said zero crossings. In some cases, curvature normalization may help improve feature pattern matching.

Pre-warp processing module 114 may also include outline alignment module 216 to align the body outlines of the corresponding images based on the curvature plots generated by outline filtering module 214. In these embodiments, outline alignment module 216 may align the body outlines of corresponding images by matching curvature peaks, such as curvature peaks at points 326 & 328 (FIG. 3D), of corresponding curvature plots. In some embodiments, outline alignment module 216 may use a pattern matching or pattern recognition technique to align the body outlines of corresponding images.

Pre-warp processing module 114 may also include spatial-transform definition module 218 to generate initial displacement flowfield map 115 to map each coordinate of one of the images based on the aligned body outlines to a corresponding coordinate of a reference image. Initial displacement flowfield map 115 may be stored in storage element 106. In these embodiments, initial displacement flowfield map 115 may define a transformation to map coordinates of one image (i.e., later-captured image 303 (FIG. 3A)) to a corresponding coordinate of another image (i.e., reference image 301 (FIG. 3A)). The application of a curvature-based mapping transform, such as initial displacement flowfield map 115 generated by spatial-transform definition module 218, to later-captured image 303 (FIG. 3A) may be used to generate pre-warped image 334 (FIG. 3E). The resulting image pair (reference image 301 (FIG. 3E) and pre-warped image 334 (FIG. 3E)) may have matched body-background edges. Although the outlines of pre-warped image 334 (FIG. 3E) and reference image 301 (FIG. 3E) are aligned, features present in the image pair, such as skin feature 333 (FIG. 3E), may remain largely unregistered (i.e., skin feature 333 in pre-warped image 334 (FIG. 3E) does not reside at the same coordinate location as in reference image 301 (FIG. 3E)). As discussed in more detail below, precision alignment and registration module 116 may be used to align skin features within the images to achieve feature registration.

Referring to FIG. 2, precision alignment and registration module 116 may use spatially and/or spectrally filtered versions 203 of corresponding images to align their internal features. In these embodiments, spatially and/or spectrally filtered versions 203 of corresponding images may be generated by image filter 202. In these embodiments, the spatial filtering performed by image filter 202 may include the use of a high-pass filter or a Harris filter. The spectral filtering performed by image filter 202 may be performed based on principal components. The filtering operations performed by image filter 202 may suppress larger-scale features within the images and may enhance smaller-scale features within the images. The spectral filtering operations may also enhance skin features due to differences in color. Image filter 202 may use as its input, captured images that have been converted to images having the predetermined DIP format by image ingestion module 204. In some embodiments, the filtering performed by image filter 202 may, among other things, suppress thin-linear features, such as hair, within an image. In some embodiments, a Harris filter may be used to achieve this suppression. In some embodiments, the parameters for image filter 202 may be varied based on pixel size (e.g. whether a pixel in an image corresponds to 0.01 mm or 0.02 mm). The parameters may be available as part of metadata associated with a captured image. Spatially and/or spectrally filtered versions 203 of the images generated by image filter 202 may be stored in data storage 106. For example, spatially and/or spectrally filtered versions 203 of the images generated by image filter 202 for both reference image 301 (FIG. 3A) and later-captured image 303 (FIG. 3A) may be stored in storage element 106.

Precision alignment and registration module 116 may include image warping module 226 to apply initial displacement flowfield map 115 to coordinates of one of the filtered images (e.g., the spatially and/or spectrally filtered version 203 of a later-captured image) to generate a pre-warped image, such as pre-warped image 334 (FIG. 3E). Precision alignment and registration module 116 may include chip-pair extractor 220 to extract chip-pairs 221 comprising corresponding chips of the pre-warped image and the corresponding filtered image (e.g. the spatially and/or spectrally filtered version 203 of the reference image 301).

Precision alignment and registration module 116 may also include offset estimator 222 to perform a correlation between the chips of chip-pairs 221 to determine a "best" spatial offset for each chip-pair. The spatial offsets may be the location of a statistically significant correlation peak and may be used to generate a displacement flowfield correction map 223.

In some embodiments, each chip may comprise a block of pixels extracted from one of the filtered images, and adjacent chips may overlap each other by one or more pixels. Chip-pair extractor 220 and offset estimator 222 may iteratively extract the chip-pairs and estimate offsets on a chip-pair per chip-pair basis (e.g., one chip-pair at time).

In some embodiments, displacement flowfield correction map 223 generated by offset estimator 222 may comprise offsets determined for each chip-pair and may identify an offset or displacement for each chip of the pre-warped image with respect a reference image. In some embodiments, the chip size for each image may be selected to correspond to the same physical dimension in the corresponding images of an image pair and may be determined based on typical body feature sizes, although the scope of the embodiments is not limited in this respect. In some embodiments, a final chip size of 3×3 mm may be used. In some embodiments, for a full-body image, up to 12 million chips or more may be extracted and processed. The physical dimension may be determined from metadata associated with the images. The metadata may include, among other things, the range at which the image was taken, focal plane information, pixel/pitch, etc, to allow image processing and feature alignment system 200 to determine the physical area that each pixel represents. In some embodiments, metadata for images may be stored with the images in data storage 106.

It should be noted that initial displacement flowfield map 115 defined by spatial-transform definition module 218 is not normally applied by image warping module 226 to color or R-G-B images, but is applied to spatially and/or spectrally filtered versions 203 of an image. In some skin-feature change detection embodiments, the application of initial displacement flowfield map 115 to an image illustrates a gross alignment of body outlines and does not necessarily achieve alignment of skin features, due to, among other things, the elasticity of the skin. Pre-warped image 334 (FIG. 3E) is provided for visualization only. Image warping module 226 applies initial displacement flowfield map 115 to the coordinates of one of the spatially and/or spectrally filtered versions 203 of images rather than the image itself.

In the embodiments discussed above, chip registration (i.e., alignment of features of corresponding chips) may be an iterative process that calculates the alignment of successively smaller image chip-pairs to define an increasingly precise spatial transformation for each pixel in one image to each pixel in a reference image. The process may start with larger chips which are extracted from a source image after passing through image warping module 226 using initial displacement flowfield map 115 generated by pre-warp processing module 114 during the pre-warp phase. For each chip-pair extracted by chip-pair extractor 220, the process attempts to locate the best alignment of the two image chips. For each chip-pair, alignment information may be stored in displacement flowfield correction map 223.

Precision alignment and registration module 116 may also include flow-field processor 224 to remove any erroneous displacements from displacement flowfield correction map 223 and to generate updated displacement flowfield map 225. Flow-field processor 224 may also be configured to remove spurious values and fill in missing data from displacement flowfield correction map 223. In some embodiments, flow-field processor 224 may identify and remove bad correlations (i.e., where the local transformation is excessive) by comparing displacements to local or nearby displacements, although the scope of the embodiments is not limited in this respect. In some embodiments, flow-field processor 224 may generate a physically-realistic transformation map as updated displacement flowfield map 225. In some embodiments, chip-pairs with statistically insignificant correlations may be removed by flow-field processor 224 and replaced by the local median (or some other modal-type estimator) of nearby registrations. Anomalies or excursions, which are registrations that result in large displacements, may be removed and replaced by the local median (or some other modal-type estimator), so that updated displacement flowfield map 225 is a more continuous, smoothly varying coordinate mapping.

Image warping module 226 may apply updated displacement flowfield map 225 to a source image, such as later-captured image 303 (FIG. 3A), to generate a registered image. In these embodiments, the reference image and registered image used by the chipping process of precision alignment and registration module 116 may both be spatially and/or spectrally filtered images. Precision alignment and registration module 116 may be configured to repeat the extraction of chips-pairs, the offset estimation, the generation of displacement flowfield correction map 223, and the generation and application of each updated displacement flowfield map 225 for successively smaller sized chips using successively generated registered images to generate final displacement flowfield map 230. Final displacement flowfield map 230 may be referred to as a transformation map and may correspond to pixel-to-pixel spatial coordinate transformation map 130 (FIG. 1). Image warping module 226 may be configured to apply final displacement flowfield map 230 to an unregistered image, such as later-captured image 303 (FIG. 3A) to generate registered image 344 (FIG. 3F). The application of final displacement flowfield map 230 represents a pixel-to-pixel transformation of an image and may be applied to the color version (e.g., images converted to the predetermined DIP format) of one of the corresponding images (i.e., later-captured image 303 (FIG. 3A) to generate registered image 344 (FIG. 3F), which may correspond to registered image 117 (FIG. 1).

In some embodiments, the chip registration process performed by precision alignment and registration module 116 may be repeated a number of times with successively smaller sized chips using chip extraction information. In some embodiments, the number of times may be specified by a user. The chip sizes may be made successively smaller until they approach the size of features desired to be identified, or until they approach the size of a pixel. In some embodiments, final displacement flowfield map 230 and/or registered image 117 (FIG. 1) may be stored in data storage 106. In some embodiments, rather than providing or storing registered image 117 (FIG. 1), such as registered image 344 (FIG. 3F), as an output, precision alignment and registration module 116 may provide final displacement flowfield map 230, which may be later applied to an image to generate a registered image, although the scope of the embodiments is not limited in this respect.

To help minimize image corruption through the multiple transformation and resampling steps performed within precision alignment and registration module 116, in some embodiments, virtual-warps may be performed and the coordinate transforms may be stored for each step and applied in succession to coordinate maps. During the final warping, transformation and resampling steps, a final composite transform may be applied to warp an original image to match its features to its corresponding mate. In these embodiments, the final warped coordinates of final displacement flowfield map 230 may be applied once at the final step of the registration process to generate registered image 344 (FIG. 3F).

In some embodiments, image warping module 226 may perform coordinate warping for each iteration of the chip registration process. A registered image, which results from each iteration of the chip registration process, may be cumulatively applied to the spatial coordinate transformation for one of the spatially and/or spectrally filtered versions of the images from the image pair. The warped coordinates may be used as input to the subsequent iteration of chip registrations. The actual color image itself does not need to be warped until after the chip registration iterations are complete and final displacement flowfield map 230 is generated in which the skin features of registered image 344 (FIG. 3F) are aligned with skin features of reference image 301 (FIG. 3F). In these embodiments, the common regions of both images (i.e. pixels which are on-body in both images) are determined via a pixel-by-pixel binary AND operation on the two body pixel masks.

Although skin-feature change-detection system 100 (FIG. 1), image processing and feature alignment system 104 (FIG.

1), and image processing and feature alignment system 200 (FIG. 2) are illustrated as having several separate functional elements (i.e., modules), one or more of the functional elements may be combined and may be implemented by combinations of software-configured elements, such as processing elements including digital signal processors (DSPs), and/or other hardware elements. For example, some elements may comprise one or more microprocessors, DSPs, application specific integrated circuits (ASICs), and combinations of various hardware and logic circuitry for performing at least the functions described herein. In some embodiments, the functional elements may refer to one or more processes operating on one or more processing elements.

Figure 4:
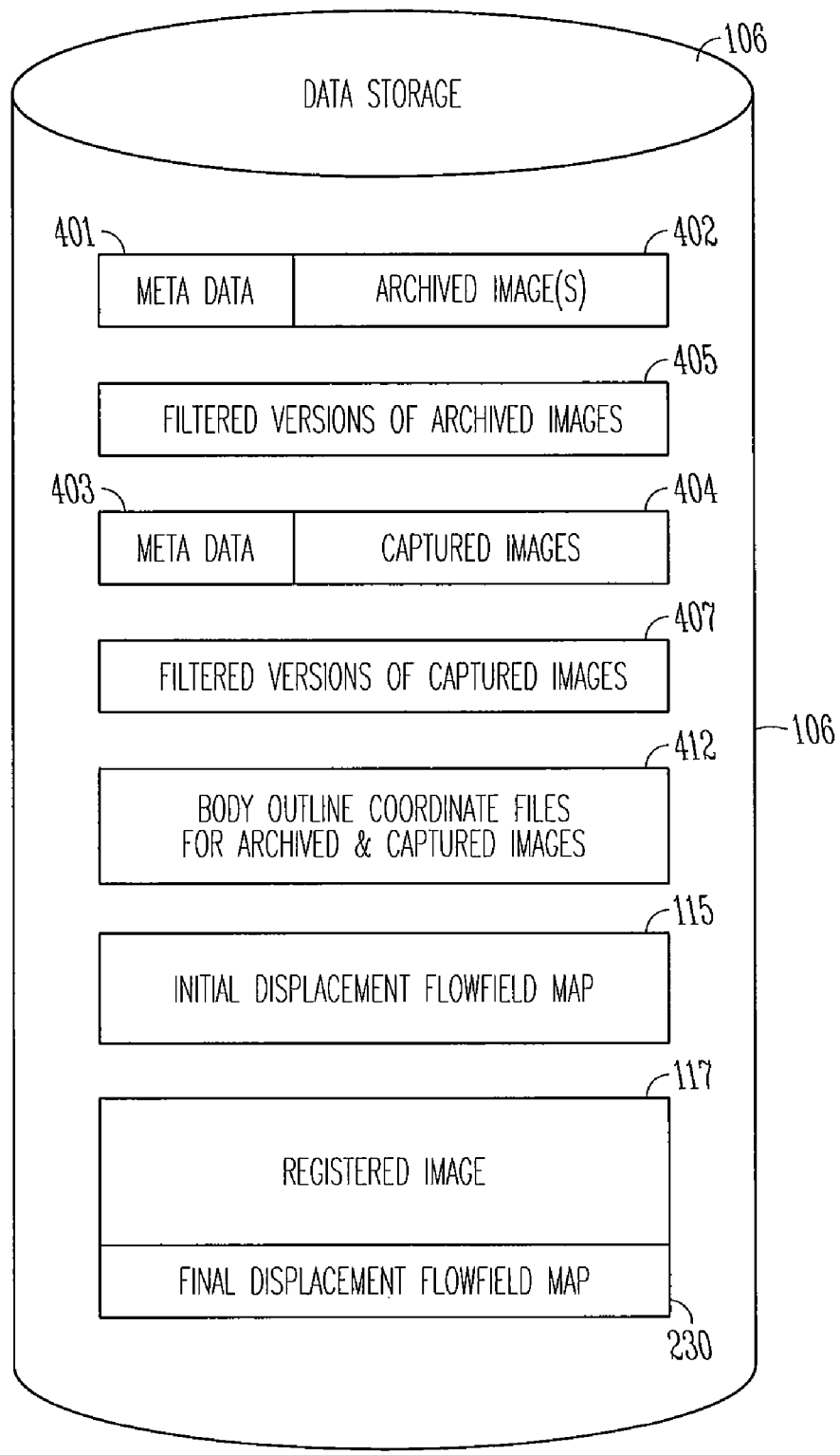
FIG. 4 illustrates a data storage element in accordance with some embodiments.

FIG. 4 illustrates a data storage element in accordance with some embodiments. Data storage element 106 may store archived images 402, which may correspond to one or more reference images, such as reference image 301 (FIGS. 3A, 3E and 3F), and metadata 401 associated with archived images 402. Data storage element 106 may also store spatially and/or spectrally filtered versions 405 of the archived images, which may be generated by image filter 202 (FIG. 2) as discussed above for use by precision alignment and registration module 116 (FIG. 2). Data storage element 106 may also store one or more captured images 404, which may correspond to later-captured image 303 (FIG. 3A), and metadata 403 associated with later-captured images 404. Data storage element 106 may also store spatially and/or spectrally filtered version 407 of a later-captured image, which may be generated by image filter 202 (FIG. 2) for use by precision alignment and registration module 116 (FIG. 2).

Data storage element 106 may also store body-outline coordinate files 412 for each corresponding image. For example, in the case of archived images 402, body-outline coordinate files 412 may be generated by outline generation module 212 (FIG. 2) as discussed above. Body-outline coordinate files 412 of corresponding images may be used for alignment with the body-outlines.

Data storage element 106 may also store initial displacement flowfield map 115, which may be generated by pre-warp processing module 114, and which may be used for gross-body alignment and generating a pre-warped image. In some embodiments, data storage element 106 may also store registered image 117 and/or final displacement flowfield map 230.

The data stored in data storage 106 is an example of some of the information that may be securely stored for a single patient in some early skin-cancer detection embodiments. In some embodiments, data storage 106 may securely store data for many patients.

Figure 5:
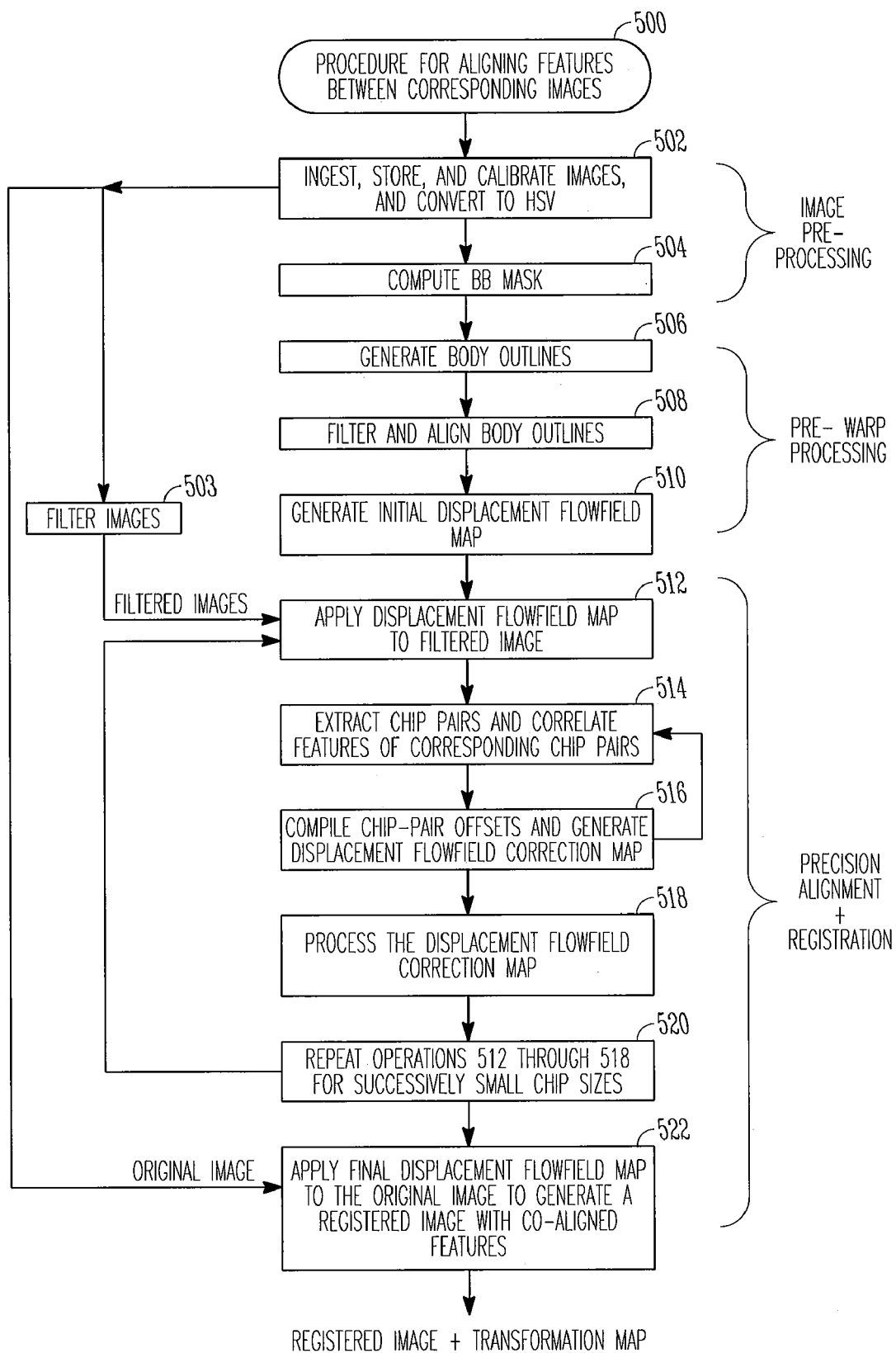
FIG. 5 is a flow chart of a procedure for aligning features between corresponding images in accordance with some embodiments.

FIG. 5 is a flow chart of a procedure for aligning features between corresponding images in accordance with some embodiments. Procedure 500 may be performed by image processing and feature alignment system 200 (FIG. 2), although this is not a requirement. Procedure 500 may be used to generate a registered image, such as registered image 344 (FIG. 3F), from a later-captured image, such as later-captured image 303 (FIG. 3A). Alternately, procedure 500 may be used to generate final displacement flowfield map, such as final displacement flowfield map 230 (FIG. 2), which may be used to generate a registered image.

Operation 502 comprises ingesting, storing and calibrating captured images to generate images in a predetermined DIP format, and converting the images to, HSV color space. In some embodiments, operation 502 may be performed by image ingestion module 204 (FIG. 2), image calibration module 206 (FIG. 2), and HSV computation module 208 (FIG. 2).

Operation 503 comprises filtering the DIP formatted images generated within operation 502 to generate spatially and/or spectrally filtered images. In some embodiments, operation 503 may be performed by image filter 202 (FIG. 2).

Operation 504 comprises computing body-background (BB) masks, such as body-background mask 313 (FIG. 3B). In some embodiments, operation 504 may be performed by BB mask computation module 210 (FIG. 2).

Operation 506 comprises generating body outlines from the BB masks. In some embodiments, operation 506 may be performed by outline generation module 212 (FIG. 2).

Operation 508 comprises filtering and aligning body outlines. In some embodiments, operation 508 may be performed by outline filtering module 214 (FIG. 2) and outline alignment module 216 (FIG. 2).

Operation 510 comprises generating an initial displacement flowfield map, such as initial displacement flowfield map 115 (FIG. 2), from the aligned body outlines. In some embodiments, operation 510 may be performed by spatial transform definition module 218 (FIG. 2).

Operation 512 comprises applying a displacement flowfield map to a filtered image to generate a warped image. In the first iteration, operation 512 may apply initial displacement flowfield map 115 (FIG. 2) generating in operation 510 to a spatially and/or spectrally filtered version 203 (FIG. 2) of a later-captured image to generate a pre-warped image. In subsequent iterations, operation 512 may apply an updated displacement flowfield map 225 (FIG. 2) generating in a subsequent iteration of operation 510 to a spatially and/or spectrally filtered version 203 (FIG. 2) of a later-captured image to generate a warped image. In some embodiments, operation 512 may be performed by image warping module 226.

Operation 514 comprises extracting chip pairs and correlating features of the corresponding chip pairs. Operation 514 may use the warped image generated in operation 512 and a spatially and/or spectrally filtered version of a reference image.

Operation 516 comprises compiling chip-pair offsets from operation 514 to generate a displacement flowfield correction map, such as displacement flowfield correction map 223 (FIG. 2). Operations 514 and 516 may be performed by chip-pair extractor 220 and offset estimator 222 (FIG. 2).

Operation 518 comprises processing the displacement flowfield correction map generated by operation 516 to generate an updated displacement flowfield map, such as updated displacement flowfield map 225 (FIG. 2). Operation 518 may be performed by flowfield processor 224 (FIG. 2).

Operation 520 comprises repeating operations 512 through 518 for successively smaller chip sizes. In these embodiments, the updated displacement flowfield map generated during each iteration by operation 518 may be applied to the spatially and/or spectrally filtered version of the later-captured image in operation 512 to generate a warped image, which may be processed in operations 514-518 until a final displacement flowfield map is generated.

Operation 522 comprises applying the final displacement flowfield map to an original image, such as later-captured image 303 (FIG. 3A) to generate a registered image, such as registered image 344 (FIG. 3F). Operation 522 may be performed by image warping module 226 (FIG. 2). The registered image and/or the final displacement flowfield map may be stored in a data storage element, such as data storage element 106 (FIG. 1) for use by change-detection system 108, although the scope of the invention is not limited in this respect. The final displacement flowfield map may correspond to pixel-to-pixel spatial transformation map 130 (FIG. 1) generated by system 104 (FIG. 1).

Although the individual operations of procedure 500 are illustrated and described as separate operations, one or more of the individual operations may be performed concurrently, and nothing requires that the operations be performed in the order illustrated. Unless specifically stated otherwise, terms such as processing, computing, calculating, determining, displaying, or the like, may refer to an action and/or process of one or more processing or computing systems or similar devices that may manipulate and transform data represented as physical (e.g., electronic) quantities within a processing system's registers and memory into other data similarly represented as physical quantities within the processing system's registers or memories, or other such information storage, transmission or display devices. Furthermore, as used herein, a computing device includes one or more processing elements coupled with computer-readable memory that may be volatile or non-volatile memory or a combination thereof.

Embodiments may be implemented in one or a combination of hardware, firmware, and software. Embodiments may also be implemented as instructions stored on a computer-readable medium, which may be read and executed by at least one processor to perform the operations described herein. A computer-readable medium may include any mechanism for storing or transmitting information in a form readable by a machine (e.g., a computer). For example, a computer-readable medium may include read-only memory (ROM), random-access memory (RAM), magnetic disk storage media, optical storage media, flash-memory devices, and others.

The Abstract is provided to comply with 37 C.F.R. Section 1.72 (b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. An image processing and feature alignment system to align skin features between corresponding images comprising a reference image and a later-captured image, the system comprising:
    a pre-warp processing module to align body outlines of the corresponding images based on curvatures; and
    a precision alignment and registration module to;
    generate an initial displacement flowfield map based on the aligned body outlines for application to a filtered version of the later-captured image to generate a pre-warped image;
    divide the pre-warped image and the reference image into a plurality of overlapping chips after body outline alignment;
    extract chip-pairs from corresponding chips of the pre-warped image and the reference image;
    perform a correlation between the extracted chip-pairs to estimate an offset for each chip-pair based on a correlation peak for use in generating an updated displacement flowfield map;
    repeat the extraction of chips-pairs, the offset estimation and the generation of the updated displacement flowfield map for successively smaller sized chips; and
    generate a pixel-to-pixel spatial coordinate transformation map to align skin features between the corresponding images based a final updated displacement flowfield map.

2. An image processing and feature alignment system to align skin features between corresponding images, the system comprising:
    a pre-warp processing module to align body outlines of the corresponding images based on curvatures; and
    a precision alignment and registration module to divide the images into a plurality of overlapping chips after body outline alignment, to perform correlations between corresponding chips, and to align skin features between the corresponding images based on the correlations,
    wherein the corresponding images comprise a reference image and a later-captured image, and
    wherein the precision alignment and registration module is configured to:
    apply an initial displacement flowfield map, generated based on the aligned body outlines, to a filtered version of the later-captured image to generate a pre-warped image;
    divide the pre-warped image and filtered version of the reference image into the plurality of overlapping chips;
    correlate skin features within corresponding chips; and
    generate a pixel-to-pixel spatial coordinate transformation map from the correlated skin features that aligns the skin features between the corresponding images.

3. The system of claim 2 wherein the precision alignment and registration module comprises an image warping module to apply the pixel-to-pixel the spatial coordinate transformation map to the later-captured image to generate a registered image, and
    wherein skin features of the registered image are aligned on an x-y coordinate basis with corresponding skin features of the reference image.

4. The system of claim 3 wherein the skin features comprise nevi, and wherein the corresponding images comprise images of at least a portion of a human body.

5. The system of claim 2 further comprising an image filter to generate the filtered versions of the reference image and the later-captured image by performing at least one of spectral filtering or spatial filtering on the corresponding images, the image filter being configured to suppress larger-scale features within the images and to enhance smaller-scale features within the images.

6. The system of claim 2 wherein the precision alignment and registration module comprises:
    an image warping module to apply an initial displacement flowfield map to the filtered version of the later-captured image to generate the pre-warped image;
    a chip-pair extractor to extract chip-pairs comprising corresponding chips from the pre-warped image and the filtered version of the reference image; and
    an offset estimator to perform a correlation between the extracted chip-pairs to determine an offset for each chip-pair based on a correlation peak for use in generating an updated displacement flowfield map.

7. The system of claim 6 wherein each chip comprises a block of one or more pixels,
    wherein adjacent chips initially overlap by one or more pixels,
    wherein the chip-pair extractor and the offset estimator iteratively extracts the chip-pairs and estimates offsets on a chip-pair per chip-pair basis, and
    wherein the precision alignment and registration module is configured to repeat the extraction of chips-pairs, the offset estimation and the application of the updated displacement flowfield map for successively smaller sized chips.

8. The system of claim 7 wherein the precision alignment and registration module further comprises a flow-field processor to generate the updated displacement flowfield map, to remove erroneous displacements and to fill in missing data from a displacement flowfield correction map generated by the offset estimator.

9. The system of claim 2 wherein the pre-warp processing module is configured to:
  generate the curvatures from body-background masks of the corresponding images;
  align the body outlines of the corresponding images based on the curvatures; and
  generate the initial displacement flowfield map to define a mapping between coordinates the corresponding images for use by the precision alignment and registration module.

10. The system of claim 9 wherein the pre-warp processing module is further configured to:
  align the body outlines of the corresponding images by matching peaks of curvature plots generated from the body outlines; and
  define an initial displacement flowfield map for the corresponding images based on the aligned body outlines,
  wherein application of the initial displacement flowfield map achieves a gross outline-alignment of the corresponding images.

11. The system of claim 9 further comprising an image pre-processing module to generate the body-background mask for the corresponding images by separating non-background pixels from background pixels in the images based on a predetermined background color.

12. The system of claim 11 wherein the image pre-processing module comprises:
  an image ingestion module to convert a captured image from a camera-raw format to a predetermined digital image processing (DIP) format, the predetermined DIP format comprising a predetermined number of bits per each color pixel;
  an image calibration module to color-balance the captured image after conversion to the predetermined DIP format; and
  a hue-saturation-value (HSV) computation module to convert the color-balanced image to HSV color space,
  wherein the reference image and the later captured image are provided in HSV color space for processing by a body-background mask computation module.

13. A method of aligning skin features between corresponding images comprising a reference image and a later-captured image performed by an image processing and feature alignment system, the method comprising:
  aligning body outlines of the corresponding images based on curvatures;
  generating an initial displacement flowfield map based on the aligned body outlines for application to a filtered version of the later-captured image to generate a pre-warped image;
  dividing the pre-warped image and the reference image into a plurality of overlapping chips after body outline alignment;
  extracting chip-pairs from corresponding chips of the pre-warped image and the reference image;
  performing a correlation between the extracted chip-pairs to estimate an offset for each chip-pair based on a correlation peak for use in generating an updated displacement flowfield map;
  repeating the extraction of chips-pairs, the offset estimation and the generation of the updated displacement flowfield map for successively smaller sized chips, and
  generating a pixel-to-pixel spatial coordinate transformation map to align skin features between the corresponding images based a final updated displacement flowfield map.

14. A method of aligning skin features between corresponding images performed by an image processing and feature alignment system, the method comprising:
  aligning body outlines of the corresponding images based on curvatures;
  dividing the images, after alignment, into a plurality of overlapping chips after body outline alignment;
  performing correlations between corresponding chips; and
  aligning skin features between the corresponding images based on the correlations,
  wherein the corresponding images comprise a reference image and a later-captured image, and
  wherein the method further comprises:
  applying an initial displacement flowfield map, generated based on the aligned body outlines, to a filtered version of the later-captured image to generate a pre-warped image;
  dividing the pre-warped image and a filtered version of the reference image into the plurality of overlapping chips;
  correlating skin features within corresponding chips; and
  generating a pixel-to-pixel spatial coordinate transformation map that aligns the skin features between the corresponding images.

15. The method of claim 14 further comprising applying the pixel-to-pixel the spatial coordinate transformation map to the later-captured image to generate a registered image,
  wherein skin features of the registered image are aligned on an x-y coordinate basis with corresponding skin features of the reference image.

16. The method of claim 14 further comprising:
  applying an initial displacement flowfield map to the filtered version of the later-captured image to generate the pre-warped image;
  extracting chip-pairs comprising corresponding chips from the pre-warped image and the filtered version of the reference image; and
  performing a correlation between the extracted chip-pairs to determine an offset for each chip-pair based on a correlation peak for use in generating an updated displacement flowfield map.

17. The method of claim 16 wherein each chip comprises a block of one or more pixels,
  wherein adjacent chips initially overlap by one or more pixels,
  wherein the chip-pairs are extracted and the offsets are estimated on a chip-pair per chip-pair basis, and
  wherein the extraction of chips-pairs, the offset estimation and the application of the updated displacement flowfield map are repeated for successively smaller sized chips.

18. The method of claim 14 further comprising:
  generating the curvatures from body-background masks of the corresponding images;
  aligning the body outlines of the corresponding images based on the curvatures; and
  generating the initial displacement flowfield map to define a mapping between coordinates the corresponding images.

19. A skin-feature change-detection system comprising:
an image processing and feature alignment system to align skin features between corresponding images comprising a reference image and a later-captured image, the system comprising a pre-warp processing module to align body outlines of the corresponding images based on curvatures and a precision alignment and registration module to generate an initial displacement flowfield map based on the aligned body outlines for application to a filtered version of the later-captured image to generate a pre-warped image, divide the pre-warped image and the reference image, after alignment, into a plurality of overlapping chips after body outline alignment; to perform a correlation between the extracted chip-pairs to estimate an offset for each chip-pair based on a correlation peak for use in generating an updated displacement flowfield map, to repeat the extraction of chips-pairs, the offset estimation and the generation of the updated displacement flowfield map for successively smaller sized chips, and to generate a pixel-to-pixel spatial coordinate transformation map to align skin features between the corresponding images based a final updated displacement flowfield map;
a change-detection system to generate change-detection reports based on a comparison of aligned skin features; and
a display system including a graphical user interface (GUI) to display the comparison of the aligned skin features.

20. A skin-feature change-detection system comprising:
an image processing and feature alignment system to align skin features between corresponding images comprising a pre-warp processing module to align body outlines of the corresponding images based on curvatures and a precision alignment and registration module to divide the images, after alignment, into a plurality of overlapping chips after body outline alignment, to perform correlations between corresponding chips, and to align skin features between the corresponding images based on the correlations;
a change-detection system to generate change-detection reports based on a comparison of aligned skin features; and
a display system including a graphical user interface (GUI) to display the comparison of the aligned skin features,
wherein the corresponding images comprise a reference image and a later-captured image, and
wherein the image processing and feature alignment system is configured to:
apply an initial displacement flowfield map, generated based on the aligned body outlines, to a filtered version of the later-captured image to generate a pre-warped image;
divide the pre-warped image and a filtered version of the reference image into the plurality of overlapping chips;
correlate skin features within corresponding chips; and
generate a pixel-to-pixel spatial coordinate transformation map from the correlated skin features that aligns the skin features between the corresponding images.

21. The system of claim 20 wherein the precision alignment and registration module comprises:
an image warping module to apply an initial displacement flowfield map to the filtered version of the later-captured image to generate the pre-warped image;
a chip-pair extractor to extract chip-pairs comprising corresponding chips from the pre-warped image and the filtered version of the reference image; and
an offset estimator to perform a correlation between the extracted chip-pairs to determine an offset for each chip-pair based on a correlation peak for use in generating an updated displacement flowfield map.

22. The system of claim 20 further comprising a pre-warp processing module configured to:
generate the curvatures from body-background masks of the corresponding images;
align the body outlines of the corresponding images based on the curvatures; and
generate the initial displacement flowfield map to define a mapping between coordinates the corresponding images for use by the precision alignment and registration module.

23. A non-transitory computer-readable medium that stores instructions for execution by one or more processors to align skin features between corresponding images by performing operations comprising:
aligning body outlines of the corresponding images based on curvatures; and
dividing the images, after alignment, into a plurality of overlapping chips after body outline alignment;
performing correlations between corresponding chips; and
aligning skin features between the corresponding images based on the correlations,
wherein the corresponding images comprise a reference image and a later-captured image, and
wherein the instructions, when further implemented cause the one or more possessors to:
apply an initial displacement flowfield map, generated based on the aligned body outlines, to a filtered version of the later-captured image to generate a pre-warped image;
divide the pre-warped image and a filtered version of the reference image into the plurality of overlapping chips;
correlate skin features within corresponding chips; and
generate a pixel-to-pixel spatial coordinate transformation map from the correlated skin features that aligns the skin features between the corresponding images.

24. The non-transitory computer-readable medium of claim 23 wherein the instructions, when further implemented cause the one or more possessors to:
generate the curvatures from body-background masks of the corresponding images;
align the body outlines of the corresponding images based on the curvatures; and
generate the initial displacement flowfield map to define a mapping between coordinates the corresponding images.

25. A precision alignment and registration module to align skin features of corresponding images comprising a reference image and a later-captured image, the module configured to generate an initial displacement flowfield map based on aligned body outlines for application to a filtered version of the later-captured image to generate a pre-warped image, divide the pre-warped image and the reference image into a plurality of overlapping chips after initial body outline alignment, to extract chip-pairs from corresponding chips of the pre-warped image and the reference image, to perform a correlation between the extracted chip-pairs to estimate an offset for each chip-pair based on a correlation peak for use in generating an updated displacement flowfield map, to repeat the extraction of chips-pairs, the offset estimation and the generation of the updated displacement flowfield map for successively smaller sized chips, and to generate a pixel-to-pixel spatial coordinate transformation map to align skin features between the corresponding images based a final updated displacement flowfield map.

26. A precision alignment and registration module to align skin features of corresponding images, the module configured to divide the images into a plurality of overlapping chips after initial body outline alignment, to perform correlations between corresponding chips, and to align skin features between the corresponding images based on the correlations,
wherein the corresponding images comprise a reference image and a later-captured image, and
wherein the precision alignment and registration module is configured to:
apply an initial displacement flowfield map, generated based on the aligned body outlines, to a filtered version of the later-captured image to generate a pre-warped image;
divide the pre-warped image and a filtered version of the reference image into the plurality of overlapping chips;
correlate skin features within corresponding chips; and
generate a pixel-to-pixel spatial coordinate transformation map that aligns the skin features between the corresponding images.

27. The precision alignment and registration module of claim 26 comprising an image warping module to apply the pixel-to-pixel the spatial coordinate transformation map to the later-captured image to generate a registered image, and
wherein skin features of the registered image are aligned on an x-y coordinate basis with corresponding skin features of the reference image.

28. The precision alignment and registration module of claim 26 further comprising:
an image warping module to apply an initial displacement flowfield map to the filtered version of the later-captured image to generate the pre-warped image;
a chip-pair extractor to extract chip-pairs comprising corresponding chips from the pre-warped image and the filtered version of the reference image; and
an offset estimator to perform a correlation between the extracted chip-pairs to determine an offset for each chip-pair based on a correlation peak for use in generating an updated displacement flowfield map.

29. The precision alignment and registration module of claim 28 wherein each chip comprises a block of one or more pixels,
wherein adjacent chips initially overlap by one or more pixels,
wherein the chip-pair extractor and the offset estimator iteratively extracts the chip-pairs and estimates offsets on a chip-pair per chip-pair basis, and
wherein the precision alignment and registration module is configured to repeat the extraction of chips-pairs, the offset estimation and the application of the updated displacement flowfield map for successively smaller sized chips.

30. The precision alignment and registration module of claim 29 further comprising a flow-field processor to generate the updated displacement flowfield map, to remove erroneous displacements and to fill in missing data from a displacement flowfield correction map generated by the offset estimator.

31. A method of aligning features of corresponding images comprising a reference image and a later-captured image, the method performed by an image processing and feature alignment system, the method comprising:
generating an initial displacement flowfield map based on aligned body outlines for application to a filtered version of the later-captured image to generate a pre-warped image,
dividing the pre-warped image and the reference image into a plurality of overlapping chips after initial body outline alignment;
extracting chip-pairs from corresponding chips of the pre-warped image and the reference image;
performing a correlation between the extracted chip-pairs to estimate an offset for each chip-pair based on a correlation peak for use in generating an updated displacement flowfield map;
repeating the extraction of chips-pairs, the offset estimation and the generation of the updated displacement flowfield map for successively smaller sized chips; and
generating a pixel-to-pixel spatial coordinate transformation map to align skin features between the corresponding images based a final updated displacement flowfield map.

32. A method of aligning features of corresponding images performed by an image processing and feature alignment system, the method comprising:
dividing the images into a plurality of overlapping chips after initial body outline alignment;
performing correlations between corresponding chips; and
aligning skin features between the corresponding images based on the correlations,
wherein the corresponding images comprise a reference image and a later-captured image, and
wherein method further comprises:
applying an initial displacement flowfield map, generated based on the aligned body outlines, to a filtered version of the later-captured image to generate a pre-warped image;
dividing the pre-warped image and a filtered version of the reference image into the plurality of overlapping chips;
correlating skin features within corresponding chips; and
generating a pixel-to-pixel spatial coordinate transformation map that aligns the skin features between the corresponding images.

33. The method of claim 32 further comprising applying the pixel-to-pixel the spatial coordinate transformation map to the later-captured image to generate a registered image, and
wherein skin features of the registered image are aligned on an x-y coordinate basis with corresponding skin features of the reference image.

34. The method of claim 32 further comprising:
applying an initial displacement flowfield map to the filtered version of the later-captured image to generate the pre-warped image;
extracting chip-pairs comprising corresponding chips from the pre-warped image and the filtered version of the reference image; and
performing a correlation between the extracted chip-pairs to determine an offset for each chip-pair based on a correlation peak for use in generating an updated displacement flowfield map.

35. The method of claim 34 wherein each chip comprises a block of one or more pixels,
wherein adjacent chips initially overlap by one or more pixels,
wherein the method includes:
iteratively extracting the chip-pairs and estimates offsets on a chip-pair per chip-pair basis; and
repeating the extracting of chips-pairs, the offset estimating and the applying of the updated displacement flowfield map for successively smaller sized chips.

36. The method of claim 35 further comprising generating the updated displacement flowfield map to remove erroneous displacements and to fill in missing data from a displacement flowfield correction map generated by the offset estimator.

* * * * *

UNITED STATES PATENT AND TRADEMARK OFFICE
CERTIFICATE OF CORRECTION

| | | |
|---|---|---|
| PATENT NO. | : 8,194,952 B2 | Page 1 of 2 |
| APPLICATION NO. | : 12/133163 | |
| DATED | : June 5, 2012 | |
| INVENTOR(S) | : Mertz et al. | |

It is certified that error appears in the above-identified patent and that said Letters Patent is hereby corrected as shown below:

IN THE SPECIFICATIONS:

In column 5, line 41, after "version", insert --of--, therefor

In column 8, line 25, delete "e.g." and insert --e.g.,--, therefor

In column 8, line 44, delete "e.g." and insert --e.g.,--, therefor

IN THE CLAIMS:

In column 13, line 66, in Claim 1, after "based", insert --on--, therefor

In column 14, line 26, in Claim 3, after "claim 2", insert --,--, therefor

In column 14, line 28, in Claim 3, before "spatial", delete "the" therefor

In column 14, line 34, in Claim 4, after "claim 3", insert --,--, therefor

In column 14, line 37, in Claim 5, after "claim 2", insert --,--, therefor

In column 14, line 44, in Claim 6, after "claim 2", insert --,--, therefor

In column 14, line 56, in Claim 7, after "claim 6", insert --,--, therefor

In column 15, line 1, in Claim 8, after "claim 7", insert --,--, therefor

In column 15, line 7, in Claim 9, after "claim 2", insert --,--, therefor

In column 15, line 18, in Claim 10, after "claim 9", insert --,--, therefor

In column 15, line 28, in Claim 11, after "claim 9", insert --,--, therefor

In column 15, line 34, in Claim 12, after "claim 11", insert --,--, therefor

In column 16, line 6, in Claim 13, after "based", insert --on--, therefor

In column 16, line 33, in Claim 15, after "claim 14", insert --,--, therefor

In column 16, line 34, in Claim 15, before "spartial", delete "the" therefor

In column 16, line 39, in Claim 16, after "claim 14", insert --,--, therefor

In column 16, line 50, in Claim 17, after "claim 16", insert --,--, therefor

In column 16, line 60, in Claim 18, after "claim 14", insert --,--, therefor

Signed and Sealed this
Second Day of October, 2012

David J. Kappos
*Director of the United States Patent and Trademark Office*

CERTIFICATE OF CORRECTION (continued)
U.S. Pat. No. 8,194,952 B2

In column 17, line 60, in Claim 21, after "claim 20", insert --,--, therefor

In column 18, line 5, in Claim 22, after "claim 20", insert --,--, therefor

In column 18, line 42, in Claim 24, after "claim 23", insert --,--, therefor

In column 19, line 1, in Claim 25, after "based", insert --on--, therefor

In column 19, line 24, in Claim 27, after "claim 26", insert --,--, therefor

In column 19, line 25, in Claim 27, before "spartial", delete "the" therefor

In column 19, line 31, in Claim 28, after "claim 26", insert --,--, therefor

In column 19, line 42, in Claim 29, after "claim 28", insert --,--, therefor

In column 19, line 55, in Claim 30, after "claim 29", insert --,--, therefor

In column 20, line 14, in Claim 31, after "based", insert --on--, therefor

In column 20, line 35, in Claim 33, after "claim 32", insert --,--, therefor

In column 20, line 41, in Claim 34, after "claim 32", insert --,--, therefor

In column 20, line 51, in Claim 35, after "claim 34", insert --,--, therefor

In column 20, line 61, in Claim 36, after "claim 35", insert --,--, therefor